United States Patent [19]

Berg

[11] Patent Number: 4,673,466

[45] Date of Patent: * Jun. 16, 1987

[54] SEPARATION OF N-HEXYL ALCOHOL FROM N-HEXYL ACETATE BY EXTRACTIVE DISTILLATION

[76] Inventor: Lloyd Berg, 1314 S. Third Ave., Bozeman, Mont. 59715

[*] Notice: The portion of the term of this patent subsequent to May 19, 2004 has been disclaimed.

[21] Appl. No.: 822,602

[22] Filed: Jan. 27, 1986

[51] Int. Cl.[4] .................. B01D 3/40; C07C 29/84
[52] U.S. Cl. .............................. 203/51; 203/60; 203/61; 203/65; 568/913
[58] Field of Search ............ 203/60, 61, 51, 18, 203/19, 14, 65, 64, 71; 568/913, 918; 560/248, 234

[56] References Cited

U.S. PATENT DOCUMENTS

| | | | |
|---|---|---|---|
| 1,859,997 | 5/1932 | Stein | 560/248 |
| 2,470,222 | 5/1949 | Patterson | 568/918 |
| 2,575,285 | 11/1951 | Carlson et al. | 203/63 |
| 4,469,905 | 9/1984 | Inwood et al. | 568/918 |
| 4,549,938 | 10/1985 | Berg et al. | 203/56 |

Primary Examiner—Wilbur Bascomb

[57] ABSTRACT n-Hexyl alcohol cannot be completely removed from n-hexyl acetate- n-hexyl alcohol - water mixtures by distillation because of the presence of the minimum ternary azeotrope. n-Hexyl alcohol can be readily removed from mixtures containing it, n-hexyl acetate and water by using extractive distillation in which the extractive distillation agent is a benzoate or a mixture of benzoates with higher boiling organic compounds. Typical examples of effective agents are benzyl benzoate; methyl benzoate and adiponitrile; ethyl benzoate, benzyl benzoate and methyl salicylate.

8 Claims, No Drawings

SEPARATION OF N-HEXYL ALCOHOL FROM N-HEXYL ACETATE BY EXTRACTIVE DISTILLATION

This application is related to application Ser. No. 06/822,604 filed Jan. 27, 1986.

FIELD OF THE INVENTION

This invention relates to a method for separating n-hexyl alcohol from n-hexyl acetate using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture n-hexyl acetate is by the catalytic esterification of n-hexyl alcohol wih acetic acid. n-Hexyl acetate (b.p.=171.5° C.), n-hexyl alcohol (b.p.=157.5° C.) and water (b.p.=100° C.) form a minimum ternary azeotrope boiling at 97.0° C. and containing 18.5 weight percent n-hexyl acetate, 52.9 wt.% n-hexyl alcohol and 28.6 wt.% water. n-Hexyl acetate forms a binary azeotrope with water boiling at 97.4° C. and containing 39 wt.% n-hexyl acetate. n-Hexyl alcohol also forms a binary minimum azeotrope with water which boils at 97.8° C. and contains 25 wt.% n-hexyl alcohol. Thus in the esterification of n-hexyl alcohol with acetic acid to form n-hexyl acetate and water, the rectification of this mixture has two binary and a ternary azeotrope to contend with, and yields the lowest boiling constituent, namely the n-hexyl acetate-n-hexyl alcohol-water ternary azeotrope. It is therefore impossible to produce n-hexyl acetate from n-hexyl alcohol and water mixtures by rectification because the lower boiling ternary azeotrope will always come off overhead as the initial product. Any mixture of n-hexyl acetate, n-hexyl alcohol and water subjected to rectification at one atmosphere pressure will produce an overhead product boiling at 97° C. and containing 18.5 wt.% n-hexyl acetate, 52.9 wt.% n-hexyl alcohol and 28.6 wt.% water. Extractive distillation would be an attractive method of effecting the separation of n-hexyl alcohol from n-hexyl acetate if agents can be found that (1) will break the n-hexyl acetate-n-hexyl alcohol-water azeotrope and (2) are easy to recover from the n-hexyl acetate, that is, form no azeotrope with n-hexyl acetate and boil sufficiently above n-hexyl acetate to make the separation by rectification possible with only a few theoretical plates.

Extractive distillation typically requires the addition of an equal amount to twice as much extractive agent as the n-hexyl acetate-n-hexyl alcohol-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with n-hexyl acetate otherwise it will form a two-phase azeotrope with the n-hexyl acetate in the recovery column and some other method of separation will have to be employed.

The breaking of this azeotrope by extractive distillation is a new concept. The closest applications of the concept might be the breaking of the methyl acetate-methanol azeotrope described by Berg & Yeh, CHEMICAL ENGINEERING COMMUNICATIONS, p.3219–3223, 1984, U.S. Pat. Nos. 4,543,164 and 4,549,938. Berg & Ratanapupech, U.S. Pat. No. 4,379,028 separated ethyl acetate from ethanol. Berg & Yeh, U.S. Pat. Nos. 4,507,176 and 4,525,245 separated n-butyl acetate from n-butanol.

TABLE 1

Effective Extractive Agents Containing Benzoates

| Compounds | Ratios | | Relative Volatilities | |
|---|---|---|---|---|
| Methyl benzoate | 1 | 6/5 | 1.50 | 1.65 |
| Methyl benzoate, Benzyl benzoate | $(1/2)^2$ | $(3/5)^2$ | 1.78 | 1.82 |
| Methyl benzoate, Butyl benzoate | $(1/2)^2$ | $(3/5)^2$ | 1.90 | 1.93 |
| Methyl benzoate, Ethyl benzoate | $(1/2)^2$ | $(3/5)^2$ | 1.91 | 1.96 |
| Methyl benzoate, Methyl salicylate | $(1/2)^2$ | $(3/5)^2$ | 2.13 | 2.04 |
| Methyl benzoate, Adiponitrile | $(1/2)^2$ | | 1.51 | — |
| Methyl benzoate, Phthalic anhydride | $(1/2)^2$ | | 1.03 | — |

TABLE 1-continued

Effective Extractive Agents Containing Benzoates

| Compounds | Ratios | | Relative Volatilities | |
|---|---|---|---|---|
| Methyl benzoate, Benzyl benzoate, Dipropylene glycol dibenzoate | (1/3)[3] | (2/5)[3] | 1.86 | 1.90 |
| Methyl benzoate, Butyl benzoate, Methyl salicylate | (1/3)[3] | (2/5)[3] | 2.22 | 2.05 |
| Methyl benzoate, Ethyl benzoate, Methyl salicylate | (1/3)[3] | (2/5)[3] | 2.41 | 2.40 |
| Methyl benzoate, Methyl salicylate, Hexahydro phthalic anhydride | (1/3)[3] | | 1.61 | |
| Benzyl benzoate | 1 | 6/5 | 2.06 | 1.86 |
| Ethyl benzoate | 1 | 6/5 | 2.24 | 2.09 |
| Ethyl benzoate, Methyl salicylate | (1/2)[2] | (3/5)[2] | 2.07 | 2.45 |
| Ethyl benzoate, Methyl salicylate, Benzyl benzoate | (1/3)[3] | (2/5)[3] | 2.18 | 2.00 |
| Methyl salicylate | 1 | 6/5 | 2.43 | 2.17 |
| Methyl salicylate, N,N—dimethylacetamide | (1/2)[2] | (3/5)[2] | 1.11 | 1.02 |

OBJECTIVE OF THE INVENTION

The object of this invention is to provide a process or method of extractive distillation that will enhance the relative volatility of n-hexyl alcohol from n-hexyl acetate in their separation in a rectification column. It is a further object of this invention to identify suitable extractive distillation agents which will eliminate the n-hexyl acetate-n-hexyl alcohol-water ternary azeotrope and make possible the production of pure n-hexyl alcohol and n-hexyl acetate by rectification. It is a further object of this invention to identify organic compounds which in addition to the above constraints, are stable, can be separated from n-hexyl acetate by rectification with relatively few theoretical plates and can be recycled to the extractive distillation column and reused with little decomposition.

SUMMARY OF THE INVENTION

The objects of the invention are provided by a process for separating n-hexyl alcohol from n-hexyl acetate which entails the use of benzoates, either alone or admixed with certain oxygenated or nitrogenous organic compounds.

DETAILED DESCRIPTION OF THE INVENTION

I have discovered that benzoates, either alone or admixed with other organic compounds, will effectively negate the n-hexyl acetate-n-hexyl alcohol-water ternary azeotrope and permit the separation of pure n-hexyl alcohol from n-hexyl acetate by rectification when employed as the agent in extractive distillation. Table 1 lists several benzoates and their mixtures and the approximate proportions that I have found to be effective. The data in Table 1 was obtained in a vapor-liquid equilibrium still. In each case, the starting material was the n-hexyl acetate-n-hexyl alcohol-water azeotrope. The ratios are the parts by weight of extractive agent used per part of n-hexyl acetate-n-hexyl alcohol-water azeotrope. The relative volatilities are listed for each of the two ratios employed. The compounds that are effective when used alone are methyl benzoate, benzyl benzoate, ethyl benzoate and methyl p-hydroxy benzoate (methyl salicylate). The compounds that are effective when mixed with methyl benzoate are benzyl benzoate, butyl benzoate, ethyl benzoate, methyl salicylate, dipropylene glycol dibenzoate, phthalic anhydride, hexahydro phthalic anhydride and adiponitrile. The compounds that are effective when mixed with ethyl benzoate are benzyl benzoate and methyl salicylate. N,N Dimethylacetamide is effective when mixed with methyl salicylate. The two relative volatilities shown in Table 1 correspond to the two different ratios investigated. For example, in Table 1, one part of methyl benzoate with one part of the n-hexyl acetate-n-hexyl alcohol-water azeotrope gives a relative volatility of 1.50, 6/5 parts of methyl benzoate give 1.65. One half part of methyl benzoate mixed with one half part of butyl benzoate with one part of the n-hexyl acetate-n-hexyl alcohol-water azeotrope gives a relative volatility of 1.90, 3./5 parts of methyl benzoate plus 3/5 parts of butyl benzoate gives 1.93. One third part of methyl benzoate plus 1/3 part of benzyl benzoate plus 1/3 part of dipropylene glycol dibenzoate with one part of the n-hexyl acetate-n-hexyl alcohol-water azeotrope gives a relative volatility of 1.86, with 2/5 parts, these three give a relative volatility of 1.90. In every example in Table 1, the starting material is the n-hexyl acetate-n-hexyl alcohol-water azeotrope which possesses a relative volatility of 1.00.

TABLE 2

Data From Run Made In Rectification Column

| Agent | Wt. % n-Hexyl Alcohol | | Relative Volatility |
|---|---|---|---|
| | Overhead | Bottoms | |
| Methylbenzoate | 97.3 | 81 | 1.605 |

Notes:
Ternary mixture comprised 12.5% n-hexyl acetate, 57.5% n-hexyl alcohol, 30% water
Agent added at 20 ml/min. Reflux rate was 10–16 ml/min.

Methyl benzoate whose relative volatility had been determined in the vapor-liquid equilibrium still, was then evaluated in a glass perforated plate rectification column possessing 4.5 theoretical plates. The n-hexyl acetate-n-hexyl alcohol-water mixture charged to the stillpot was 12.5% n-hexyl acetate, 57.5% n-hexyl alcohol and 30% water. The ratio of n-hexyl alcohol to n-hexyl acetate in the overhead is 36 which is greater than 0.35 and the results are presented in Table 2. Without the extractive agent, the overhead would approach the azeotrope whose ratio of n-hexyl alcohol to n-hexyl acetate is 2.86. This proves that the extractive agent is negating the azeotrope and makes the rectification proceed as if the azeotrope no longer existed and brings the more volatile components, n-hexyl alcohol and water, out as overhead products. It is my belief that this is the first time that this has been accomplished for this azeotrope.

The data in Table 2 was obtained in the following manner. The charge was brought to boiling and after a half hour of operation in the 4.5 theoretical plate column to establish equilibrium throughout, methylbenzoate at 95° C. and 10–16 ml/min. was pumped in. The rectification was continued for 1¼ hours with sampling of the overhead and bottoms after 75 minutes. The analysis is shown in Table 2 and was 97.3% n-hexyl alcohol in the overhead and 81% n-hexyl alcohol in the bottoms, both on a water-free basis, which gives a relative volatility of 1.605 of n-hexyl alcohol to n-hexyl acetate. This indicates that the ternary azeotrope has been negated and the separation accomplished. The n-hexyl alcohol comes off in the form of its binary azeotrope with water which on condensation, immediately forms two layers. The solubility of n-hexyl alcohol in liquid water is only 0.6%.

THE USEFULNESS OF THE INVENTION

The usefulness or utility of this invention can be demonstrated by referring to the data presented in Tables 1 and 2. All of the successful extractive distillation agents show that n-hexyl alcohol n-hexyl acetate and water can be separated from their ternary azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity n-hexyl alcohol from any mixture of these three including the ternary azeotrope. The stability of the compounds used and the boiling point difference is such that complete recovery and recycle is obtainable by a simple distillation and the amount required for make-up is small.

WORKING EXAMPLES

Example 1

The n-hexyl acetate-n-hexyl alcohol-water azeotrope is 18.5 wt.% n hexyl acetate, 52.9 wt.% n-hexyl alcohol and 28.6 wt.% water. Fifty grams of the n-hexyl acetate-n-hexyl alcohol-water azeotrope and fifty grams of methyl benzoate were charged to an Othmer type vapor-liquid equilibrium still and refluxed for 10 hours. Analysis of the vapor and liquid by gas chromatography gave a vapor composition of 60.0% n-hexyl alcohol, 40.0% n-hexyl acetate, a liquid composition of 50.0% n-hexyl alcohol, 50.0% n-hexyl acetate. This indicates a relative volatility for 1.50. Ten grams of methyl benzoate were added and refluxing continued for another 12 hours. Analysis indicated a vapor composition of 56.9% n-hexyl alcohol, 43.1% n-hexyl acetate; a liquid composition of of 44.4% n-hexyl alcohol, 55.6% n-hexyl acetate which is a relative volatility of 1.65.

Example 2

Fifty grams of the n-hexyl acetate-n-hexyl alcohol-water azeotrope, 25 grams of methyl benzoate and 25 grams of butyl benzoate were charged to the vapor-liquid equilibrium still and refluxed for 12 hours. Analysis indicated a vapor composition of 76.1% n-hexyl alcohol, 23.9% n-hexyl acetate; a liquid composition of 62.7% n-hexyl alcohol, 37.3% n-hexyl acetate which is a relative volatility of 1.90. Five grams each of methyl benzoate and butyl benzoate were added and refluxing continued for another 12 hours. Analysis indicated a vapor composition of 74.4% n-hexyl alcohol, 25.6% n-hexyl acetate; a liquid composition of 70.0% n-hexyl alcohol, 30.0% of n-hexyl acetate which is a relative volatility of 1.93.

Example 3

Fifty grams of the n-hexyl acetate-n-hexyl alcohol-water azeotrope, 17 grams each of methyl benzoate, butyl benzoate and dipropylene glycol dibenzoate were charged to the vapor-liquid equilibrium still and refluxed for eleven hours. Analysis indicated a vapor composition of 66.7% n-hexyl alcohol, 33.3% n-hexyl acetate, a liquid composition of 51.9% n-hexyl alcohol, 48.1% n-hexyl acetate which is a relative volatility of 1.86. Three grams each of methyl benzoate, butyl benzoate and dipropylene glycol dibenzoate and refluxing continued for another 11 hours. Analysis indicated a vapor composition of 62.3% n-hexyl alcohol, 37.7% n-hexyl acetate; a liquid composition of 46.5% n-hexyl alcohol, 53.5% n-hexyl acetate which is a relative volatility of 1.90.

Example 4

A glass perforated plate rectification column was calibrated with ethylbenzene and p-xylene which possesses a relative volatility of 1.06 and found to have 4.5 theoretical plates. A solution comprising 50 grams of n-hexyl acetate, 230 grams of n-hexyl alcohol and 120 grams of water was placed in the stillpot and heated. When refluxing began, an extractive agent consisting of pure methyl benzoate was pumped into the column at a rate of 20 ml/min. The temperature of the extractive agent as it entered the column was 95° C. After establishing the feed rate of the extractive agent, the heat input to the n-hexyl acetate-n-hexyl alcohol-water in the stillpot was adjusted to give a total reflux rate of 10-16 ml/min. After 75 minutes of steady operation, the overhead and bottoms samples of approximately two ml. were collected and analysed using gas chromatography. The overhead analysis was 97.3% n-hexyl alcohol, 2.7% n-hexyl acetate. The bottoms analysis was 81% n-hexyl alcohol, 19% n-hexyl acetate. Using these compositions in the Fenske equation, with the number of theoretical plates in the column being 4.5, gave an average relative volatility of 1.605 for each theoretical plate.

The nature of the present invention having been described, what I wish to claim as new and useful and secure by Letters Patent is:

1. A method for recovering n-hexyl alcohol from a mixture of n-hexyl acetate, n-hexyl alcohol and water which comprises distilling a mixture of n-hexyl acetate, n-hexyl alcohol and water in a rectification column in the presence of about one part of an extractive agent per part of n-hexyl acetate-n-hexyl alcohol-water mixture, recovering n-hexyl alcohol and water as overhead product and obtaining the n-hexyl acetate and the extractive agent from the stillpot, the extractive agent comprises a benzoate containing from eight to fourteen carbon atoms.

2. The method of claim 1 in which the extractive agent comprises methyl benzoate.

3. The method of claim 1 in which the extractive agent comprises benzyl benzoate.

4. The method of claim 1 in which the extractive agent comprises ethyl benzoate.

5. The method of claim 1 in which the extractive agent comprises methyl p-hydroxybenzoate.

6. The method of claim 1 in which the extractive agent comprises methyl benzoate and at least one material from the group consisting of benzyl benzoate, butyl benzoate, ethyl benzoate, dipropylene glycol dibenzoate, methyl salicylate, phthalic anhydride, hexahydro phthalic anhydride and adiponitrile.

7. The method of claim 1 in which the extractive agent comprises ethyl benzoate and at least one material from the group consisting of benzyl benzoate and methyl salicylate.

8. The method of claim 1 in which the extractive agent comprises a mixture of methyl p-hydroxybenzoate and N,N-dimethylacetamide.

* * * * *